(12) United States Patent
Benecke et al.

(10) Patent No.: US 9,260,372 B2
(45) Date of Patent: Feb. 16, 2016

(54) METHOD FOR THE PRODUCTION OF POLYOLS AND USES THEREOF

(71) Applicant: PETROLIAM NASIONAL BERHAD, Kuala Lumpur (MY)

(72) Inventors: Herman Paul Benecke, Columbus, OH (US); Daniel B. Garbark, Blacklick, OH (US)

(73) Assignee: Petroliam Nasional Berhad, Kuala Lumpur (MY)

( * ) Notice: Subject to any disclaimer, the term of this patent is extended or adjusted under 35 U.S.C. 154(b) by 0 days.

(21) Appl. No.: 14/381,539

(22) PCT Filed: Feb. 28, 2013

(86) PCT No.: PCT/MY2013/000039
§ 371 (c)(1),
(2) Date: Aug. 27, 2014

(87) PCT Pub. No.: WO2013/129908
PCT Pub. Date: Sep. 6, 2013

(65) Prior Publication Data
US 2015/0005520 A1  Jan. 1, 2015

Related U.S. Application Data

(60) Provisional application No. 61/604,303, filed on Feb. 28, 2012.

(51) Int. Cl.
*C07C 67/08* (2006.01)
*C07C 29/15* (2006.01)
*C07C 51/34* (2006.01)
(Continued)

(52) U.S. Cl.
CPC ............ *C07C 67/08* (2013.01); *C07C 29/15* (2013.01); *C07C 51/34* (2013.01); *C07C 69/003* (2013.01); *C11C 3/003* (2013.01); *C11C 3/006* (2013.01); *C11C 3/02* (2013.01); *C11C 3/10* (2013.01)

(58) Field of Classification Search
None
See application file for complete search history.

(56) References Cited

U.S. PATENT DOCUMENTS

| 667,043 A | 1/1901 | Steep |
| 2,401,338 A | 6/1946 | Dunmire |

(Continued)

FOREIGN PATENT DOCUMENTS

| AU | 165032 | 2/1954 |
| CN | 102010772 A | 4/2011 |

(Continued)

OTHER PUBLICATIONS

International Search Report and Written Opinion for PCT/MY2013/000039 mailed Jun. 27, 2013.

(Continued)

*Primary Examiner* — Yate K Cutliff
(74) *Attorney, Agent, or Firm* — LeClairRyan, a Professional Corporation

(57) ABSTRACT

The present invention provides a pretreatment method to reduce saturated fatty acids of fatty acids used as feedstock when preparing ester polyols. The range of feedstock includes non-fractionated to fully fractionated feedstock. Performing some fractionation by distillation of the fatty acids derived from feedstock eliminates the need to fractionate the various ozone esters from each other before esterification. Further, the approach of the present invention is more economical and efficient than the conventional method of fractionation by crystallization.

18 Claims, 3 Drawing Sheets

(51) Int. Cl.
*C11C 3/10* (2006.01)
*C11C 3/00* (2006.01)
*C11C 3/02* (2006.01)
*C07C 69/003* (2006.01)

(56) References Cited

U.S. PATENT DOCUMENTS

| | | | |
|---|---|---|---|
| 2,566,559 | A | 9/1951 | Dolnick et al. |
| 2,813,113 | A | 11/1957 | Goebel et al. |
| 2,997,493 | A | 8/1961 | Huber |
| 4,061,581 | A | 12/1977 | Leleu et al. |
| 4,298,730 | A | 11/1981 | Galleymore et al. |
| 4,313,890 | A * | 2/1982 | Chu et al. ............... 554/162 |
| 5,773,256 | A | 6/1998 | Pelenc et al. |
| 5,773,391 | A | 6/1998 | Lawate et al. |
| 6,107,500 | A | 8/2000 | Prossel et al. |
| 7,125,950 | B2 | 10/2006 | Dwan'Isa et al. |
| 7,192,457 | B2 | 3/2007 | Murphy et al. |
| 7,589,222 | B2 | 9/2009 | Narayan et al. |
| 2004/0167343 | A1 | 8/2004 | Halpern et al. |
| 2005/0112267 | A1* | 5/2005 | Kian et al. ............... 426/602 |
| 2006/0194974 | A1 | 8/2006 | Narayan et al. |
| 2009/0216040 | A1* | 8/2009 | Benecke et al. ............ 560/155 |
| 2010/0087350 | A1 | 4/2010 | Sonnenschein et al. |
| 2010/0117022 | A1 | 5/2010 | Carr et al. |
| 2011/0269979 | A1* | 11/2011 | Benecke et al. ............. 554/69 |
| 2011/0269981 | A1 | 11/2011 | Benecke et al. |
| 2011/0269982 | A1 | 11/2011 | Benecke et al. |
| 2012/0184758 | A1 | 7/2012 | Krull et al. |
| 2015/0018260 | A1 | 1/2015 | Benecke et al. |
| 2015/0018444 | A1 | 1/2015 | Garbark et al. |
| 2015/0080599 | A1 | 3/2015 | Garbark et al. |
| 2015/0087850 | A1 | 3/2015 | Benecke et al. |

FOREIGN PATENT DOCUMENTS

| | | | |
|---|---|---|---|
| EP | 0010333 | A1 | 4/1980 |
| EP | 1260497 | A2 | 11/2002 |
| EP | 1529828 | A1 | 5/2005 |
| EP | 1533360 | A1 | 5/2005 |
| KR | 10-2008-0023290 | A | 3/2008 |
| MY | 140833 | A | 1/2010 |
| WO | 9324585 | A1 | 12/1993 |
| WO | 0039068 | A1 | 7/2000 |
| WO | 2006093874 | A2 | 9/2006 |
| WO | 2007027223 | A2 | 3/2007 |
| WO | 2010-078493 | A1 | 7/2010 |
| WO | 2010/085545 | A1 | 7/2010 |
| WO | 2010078491 | A1 | 7/2010 |
| WO | 2010078493 | A1 | 7/2010 |
| WO | 2010078498 | A1 | 7/2010 |
| WO | 2010078505 | A1 | 7/2010 |
| WO | 2013129907 | A1 | 9/2013 |
| WO | 2013129908 | A1 | 9/2013 |
| WO | 2013129909 | A1 | 9/2013 |
| WO | 2013129910 | A1 | 9/2013 |
| WO | 2013129911 | A1 | 9/2013 |
| WO | 2014133380 | A8 | 9/2014 |

OTHER PUBLICATIONS

Ackman et al., "Ozonolysis of Unsaturated Fatty Acids. I. Ozonolysis of Oleic Acid," Can. J. Chem., 39:1956-1963 (1961).

Yunus et al., "Preparation and Characterization of Trimethylolpropane Esters from Palm Kernel Oil Methyl Esters," J. Oil Palm Research, 15(2):42-49 (2003).

Spyros, A., "Quantitative Determination of the Distribution of Free Hydroxylic and Carboxylic Groups in Unsaturated Polyester and Alkyd Resins by 31 P-NMR Spectroscopy," J. Appl. Polym. Sci., 83:1635-1642 (2002).

PCT International Search Report and Written Opinion for International Patent Application No. PCT/MY2013/000038 (Jun. 27, 2013).

PCT International Search Report and Written Opinion for International Patent Application No. PCT/MY2013/000039 (Jun. 27, 2013).

PCT International Search Report and Written Opinion for International Patent Application No. PCT/MY2013/000040 (Jun. 28, 2013).

PCT International Search Report and Written Opinion for International Patent Application No. PCT/MY2013/000041 (Jun. 28, 2013).

PCT International Search Report and Written Opinion for International Patent Application No. PCT/MY2013/000042 (Jun. 28, 2013).

International Preliminary Report on Patentability for International Patent Application No. PCT/MY2013/000038 (Sep. 12, 2014).

International Preliminary Report on Patentability for International Patent Application No. PCT/MY2013/000039 (Sep. 12, 2014).

International Preliminary Report on Patentability for International Patent Application No. PCT/MY2013/000040 (Sep. 12, 2014).

International Preliminary Report on Patentability for International Patent Application No. PCT/MY2013/000041 (Sep. 12, 2014).

International Preliminary Report on Patentability for International Patent Application No. PCT/MY2013/000042 (Sep. 12, 2014).

Third Party Submission for U.S. Appl. No. 14/381,554 dated Jul. 13, 2015.

Extended European Search Report for EP13755362.4 dated Aug. 21, 2015.

Extended European Search Report for EP13754711.3 dated Sep. 3, 2015.

PCT International Search Report and Written Opinion corresponding to PCT/MY2014/000026, filed Feb. 28, 2014 (mailed May 21, 2014).

Translated Office Action for Chinese Application No. 201380022561.5, mailed Sep. 6, 2015.

Search Report and Written Opinion for Singapore Application No. 11201405261T, mailed Sep. 10, 2015.

Search Report and Written Opinion for Singapore Application No. 11201405268P, mailed Oct. 1, 2015.

Dffice Action for U.S. Appl. No. 14/381,530 dated Dec. 10, 2015.

Gmehling et al., "Azeotropic Data for Binary Mixtures", Handbook of Chemistry and Physics (96th Edition, 2015-2016), pp. 6-210 to 6-228.

* cited by examiner

METHOD FOR THE PRODUCTION OF POLYOLS AND USES THEREOF

This application is a national stage application under 35 U.S.C. 371 from PCT/MY2013/000039, filed Feb. 28, 2013, which claims the benefit of U.S. Provisional Patent Application Ser. No. 61/604,303, filed Feb. 28, 2012, each of which is hereby incorporated by reference in its entirety.

FIELD OF THE INVENTION

The present invention relates to methods for the purification of fatty acid alkyl esters and ozone esters leading to purified ester polyols.

BACKGROUND OF THE INVENTION

Ester polyols are very useful for the production of polyurethane-based coatings and foams, as well as, polyester applications. The present invention provides a process using renewable resources, such as, oils and fats, fatty acids, and fatty acid alkyl esters derived from plants and animals to produce polyurethane foams and lubricants. Some chemicals derived from vegetable oils and animal fats are oleochemicals, which can have structures similar to petrochemicals, which are chemicals derived from petroleum. As the price of crude oil increases, an increase in demand from oleochemicals is expected.

Plant oils and animal fats are primarily composed of triglycerides that can be readily hydrolyzed to their component fatty acids and glycerin. Fatty acids obtained from either source are typically composed of mixtures of saturated and unsaturated fatty acids and fatty acids obtained from plant oils are usually richer in unsaturated fatty acids. Saturated fatty acids typically have higher melting points and much lower solubilities in a variety of solvents and other components than unsaturated fatty acids and partial removal of saturated fatty acids is practiced in certain applications. As described in U.S. Pat. No. 2,813,113 and related patents, fatty acids may be subjected to oxidative ozonolysis which involves an initial reaction with ozone to form intermediate ozonides followed by the oxidation of such intermediates with oxygen and a catalyst. This process generates mixtures of monoacids and diacids which are commonly called ozone acids. The oxidative ozonolysis process cleaves all double bonds in unsaturated fatty acids and introduces carboxylic acid functionality at all original double-bonded carbon atoms present in unsaturated fatty acids. Based on U.S. Pat. No. 2,813,113, the ozonolysis stage must be performed at relatively low temperatures and the viscosity of the intermediate ozonides is advantageously kept below minimum values at low temperatures. Typically a solvent is used in the oxidative ozonolysis process to help reduce reaction mixture viscosities. Since the viscosities of unsaturated fatty acids can be less than the viscosity of the corresponding saturated fatty acid, partial removal of saturated fatty acids can result in further reduction of reaction viscosity. Also, partial removal of saturated fatty acids, which do not undergo reaction with ozone or oxygen, before oxidative ozonolysis can increase the efficiency of mixing and reaction of unsaturated fatty acids with gaseous ozone and oxygen during the two-stage oxidative ozonolysis process. Removal of non-reactive saturated fatty acids prior to oxidative ozonolysis also can reduce the reactor size required to produce a certain amount of cleaved product. Thus, there is a rationale for partial removal of saturated fatty acids from unsaturated fatty acid feedstocks before undergoing oxidative ozonolysis.

A common industrial method to purify fatty acids involves fractional crystallization of saturated fatty acids from unsaturated fatty acids at relatively low temperatures either without or with the aid of solvents. This approach is based on the fact that saturated fatty acids typically have higher melting points and lower solubilities in other components than unsaturated fatty acids. When solvents are not used, mixtures of fatty acids are first heated so that the sample is fully liquid and these samples are then slowly cooled to temperatures of about 35° F. which results in partial crystallization of saturated fatty acids while the unsaturated fatty acids mainly remain in the liquid state. The solidified saturated fatty acids are then typically removed by filtration involving application of pressure to squeeze the liquid from the solid mass. Disadvantages of this approach are that the lower temperature must be reached slowly to obtain effective selective fractionation and this process results in only partial fractionation of saturated fatty acids from unsaturated fatty acids. Fractional crystallization has also been performed by initially dissolving fatty acid mixtures in solvents such as methanol or acetone and decreasing the temperature to −15° C. when methanol is used and −50° C. when acetone is used. A disadvantage of this approach is that these flammable solvents must be recovered and recycled to enhance the economics of this process. Tallow, a common source of fatty acids, consists of about 47 percent of the mono-unsaturated fatty acid oleic acid. When solvent-based crystallization techniques are applied to tallow, the product recovered from solvent contains 70-80 percent oleic acid.

The conventional method of fractionation of fatty acids by crystallization is shown in FIG. 1. FIG. 1 also shows the oxidative ozonolysis of the fractionated fatty acids to form a mixture of ozone acids that are then converted to product ester polyols. Another reason to remove saturated fatty acids from mixtures of saturated and unsaturated fatty acids is the enhanced performance of ester polyols containing reduced quantities of saturated fatty acids.

SUMMARY OF THE INVENTION

In the present invention, a polyol or derived lubricant base stock is comprised of ester polyols formed from the reaction product of ozone esters and excess primary polyol. The intermediate fatty acid alkyl esters or ozone esters have a reduced saturated fatty acid content due to pre-treatment steps that partially removes saturated fatty acids or saturates by the process of fractional distillation, which improves the viscosity of the ozone esters and also improves the performance of resulting ester polyols and derived lubricant base stocks.

The approach and methodology of the present invention is to use fractional distillation of appropriate feedstock to provide more effective and versatile approaches to fractionate fatty acids than the currently used crystallization approaches. In accordance to this invention, fractional distillation is applied to fatty acid alkyl esters which are obtained by hydrolysis of various triglyceride feedstocks, including palm oil, oleins, and palm fatty acid distillate (PFAD), etc. to produce fatty acids. The fatty acids are then esterified with monoalcohols (e.g., 1-butanol) to produce fatty acid alkyl esters. Alternatively, the triglycerides, such as, palm oil, olein, etc. can be directly transesterified with monoalcohols to produce fatty acid alkyl esters. Further, the present invention allows the use of a wide range of palm-based feedstock including palm distillates (e.g., PFAD and PKFAD), which are considered to be byproducts and low-value materials derived from the processing activities of palm oil mills. Fractional distillation of these fatty acid alkyl esters is believed to be appreciably more economical and more effective than the currently-used crystallization processes. Fractional distillation reduces the level of saturated fatty acid alkyl esters (palmitic and stearic alkyl esters) and therefore maintains the desired level of fluidity (low viscosity), which is critical to the oxidative ozonolysis process step. Due to the significantly decreased viscosities of esters versus viscosities of the corresponding acids, use of additional solvent during oxidative ozonolysis may not be required.

Another approach of this invention involves the formation of fatty acid alkyl esters from the same sources listed above but these fatty acid alkyl esters are used directly in the oxidative ozonolysis process to produce ozone esters without fractionation. Again due to the low viscosities of esters versus that of the corresponding carboxylic acids, the use of additional solvent during oxidative ozonolysis may not be required. In this approach, the mixture of ozone esters are fractionally distilled and it is expected that this distillation will be effective since the saturated fatty acids alkyl esters (mainly palmitic and stearic alkyl esters) will not undergo cleavage with ozone while the unsaturated fatty acid alkyl esters will undergo cleavage to smaller products. Fractional distillation modelling by ChemCad indicates the feasibility of separation of these smaller components from palmitic and stearic alkyl esters.

Another object of the present invention is to produce ester polyols for use in polyurethane rigid and flexible foams and as intermediate for the production of base stock for lubricant applications

BRIEF DESCRIPTION OF THE FIGURES

The accompanying figures, which are incorporated in and constitute a part of this specification, illustrate aspects of the invention and, together with a general description of the invention given above, and the detailed description given below, serve to explain the invention.

DETAILED DESCRIPTION OF THE INVENTION

Figure 1:
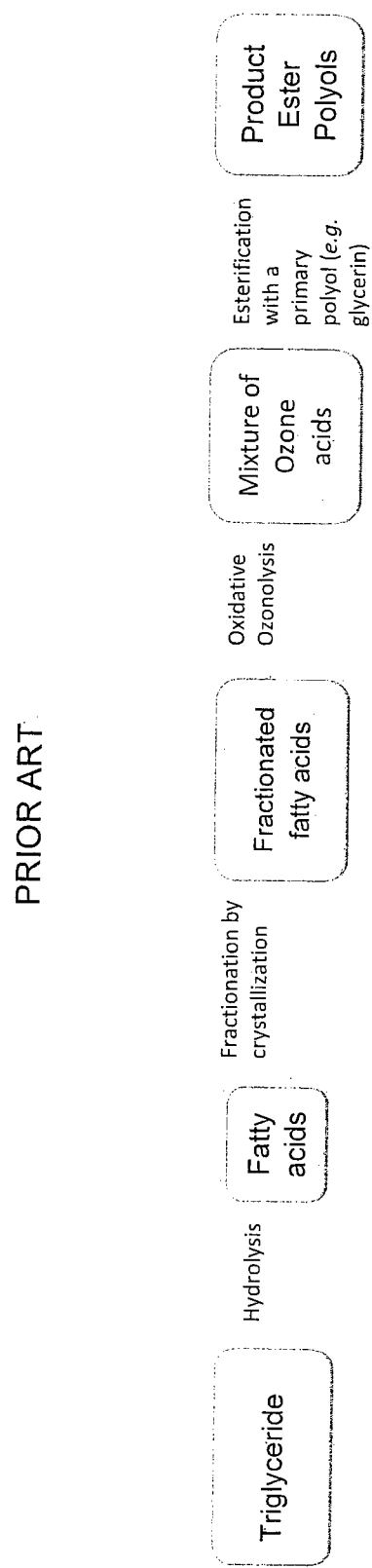
FIG. 1 is a simplified block diagram illustrating the conventional process of producing ester polyols via ozonolysis of a mixture of ozone acids. The fatty acids are fractionated by crystallization, followed by oxidative ozonolysis to produce ozone acids that are esterified with primary polyols to form product ester polyols.

The present invention relates to a method for the preparation of polyols. An aspect of the present invention relates to the pre-treatment or process steps performed on the feedstock that enables a wide range of feedstock to be used to produce ester polyols.

Such treatment steps relates to the hydrolysis of triglyceride-based feedstock to produce the fatty acids and followed by esterification with a monoalcohol to produce a fatty acid alkyl ester, which is the main building molecule used to produce ozone esters via the oxidative ozonolysis. Alternatively, the triglyceride-based feedstock, such as, palm oil and olein can be trans-esterified with a monoalcohol to produce a fatty acid alkyl ester.

The resulting fatty acid alkyl esters may undergo fractionation by distillation to produce fractionated fatty acid alkyl esters. This approach reduces the level of saturation in the fatty acid alkyl esters, specifically the level of palmitic and stearic alkyl esters. This corresponds to reducing the viscosities of the fatty acid alkyl esters, which is essential to the oxidative ozonolysis reaction. Due to the decreased viscosities of the esters compared to the viscosities of the corresponding acids, use of an additional solvent during oxidative ozonolysis may not be required. Alternatively, when these esters are used, less additional solvent may be required.

In another approach, the fatty acid alkyl esters are used directly in the oxidative ozonolysis process to produce a mixture of ozone esters. The mixture of ozone esters is fractionated by distillation to produce a fractionated mixture where the saturated fraction corresponding to palmitic and stearic alkyl esters is partially removed. The resulting ozone esters produce higher performing ester polyols, especially in lubricant applications compared to ozone esters prepared from non-fractionated acids.

The feasibility of fractionation by distillation is predicted by ChemCad simulations.

Although various grades of palm oil and palm olein can be used to produce the ester polyols, the present invention allows us to utilize the full composition of low value materials derived from the processing activities of palm oil mills, such as, palm fatty acid distillate (PFAD) and palm kernel fatty acid distillate (PKFAD). This illustrates the advantages of performing the treatment processes to use a wider range of feedstock.

Another advantage of the present invention relates to the oxidative ozonolysis process, where the carbon atoms of all available double bonds in the molecular structure of the unsaturated fatty acid alkyl ester are converted to carboxylic acid groups while maintaining the fatty acid alkyl ester functionality at the terminal position of these starting materials. This mixture is referred to as ozone esters. In the present invention, the acid functionality in ozone esters is esterified with primary polyols and the ester functionality is simultaneously transesterified with primary polyols in one step to form product ester polyols. The present invention only requires one mole of ozone per mole of double bond. Oxidative ozonolysis of the fatty acid alkyl esters cleaves the double bond of the fatty acid alkyl esters and produces a mixture of ozone esters. For example, an oleic acid alkyl ester will be converted to the half ester (hemiester) of azelaic acid and pelargonic acid esters, while the less abundant linoleic and linolenic esters found in any palm-based materials will be converted to the half ester of azelaic acid, and hexanoic acid and the half ester of azelaic acid and propionic acid, respectively and minor amounts of other acids. All of these conversions will produce a mixture of ozone esters that do not contain any double bonds, which can be a point of attack for further oxidation to take place. The lack of double bonds is advantageous in lubricant applications, specifically for increased oxidative stability.

FIG. 1 shows the conventional method of producing an ester polyol as commonly practiced in oleochemical industries. FIG. 1 shows a simplified block diagram illustrating the conventional process of producing an ester polyol via oxidative ozonolysis of fractionated fatty acids. The mixture of ozone acids formed through this ozonolysis is then esterified with an excess of primary polyol, such as, glycerin to produce an ester polyol. The feedstock used is typically a source of triglycerides and more specifically palm oil or olein. After the hydrolysis of the palm oil or olein, the fatty acids are then fractionated by crystallization to form a mixture of fatty acids (containing an increased concentration of oleic acid).

Ozone is then reacted with this fatty acid mixture until all double bonds are reacted to produce a mixture of ozone acids sparged into the reactor until breakthrough is achieved (at the time when ozone is detected escaping the reaction vessel. Nonanoic (pelargonic acid), which is a product of oxidative ozonolysis, is typically used as a diluent during the ozonolysis to reduce the viscosity of the reactant mixtures.

Figure 2:
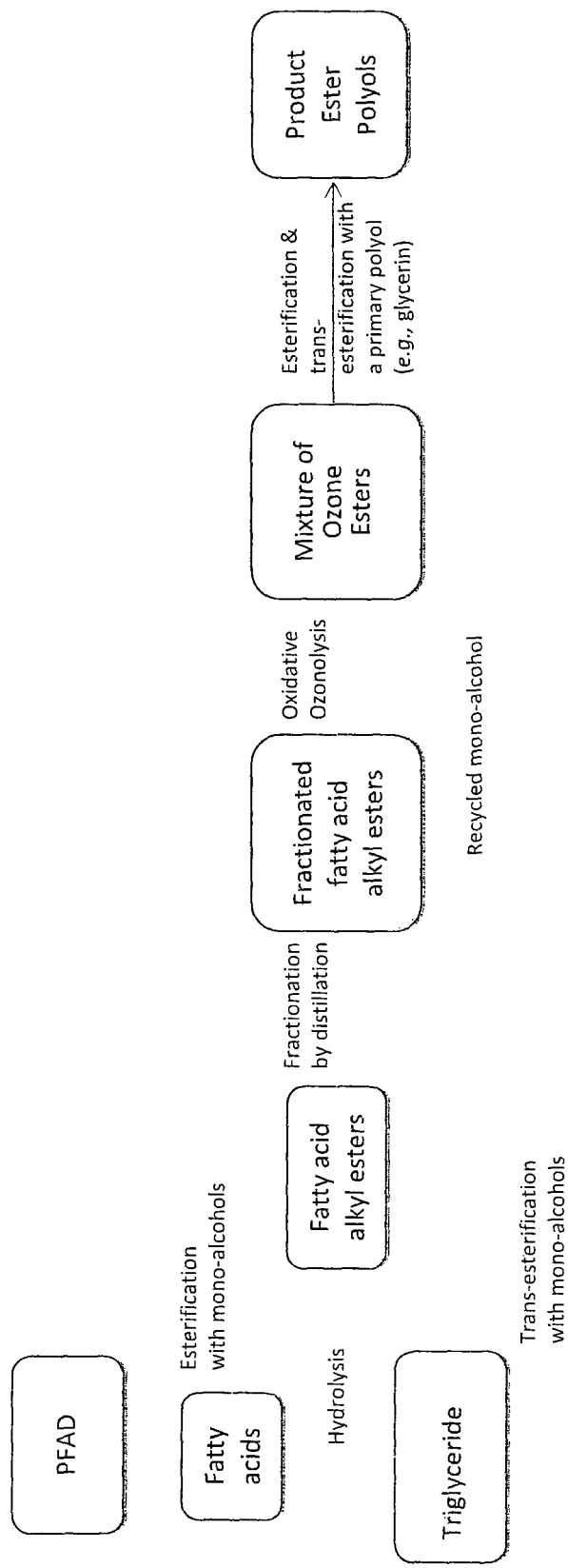
FIG. 2 is a simplified block diagram illustrating the general process of producing ester polyols via fractionation of fatty acid alkyl esters by distillation to reduce the saturation level in the ester mixture. The fractionated fatty acid alkyl esters are subjected to oxidative ozonolysis to form a mixture of ozone esters. The mixture of ozone esters is then simultaneously esterified and trans-esterified with a primary polyol (e.g., glycerin) to form an ester polyol.

FIG. 2 illustrates a simplified block diagram depicting the process steps adopted by the present invention to produce an ester polyol via oxidative ozonolysis of fractionated fatty acid alkyl esters. Again, the typical feedstock, such as, palm oil, olein, or palm fatty acid distillates (PFAD) when subjected to hydrolysis provide a source of fatty acids. Generally, the feedstock is hydrolyzed to generate fatty acids. The fatty acids are then subjected to esterification with monoalcohols to produce fatty acid alkyl esters. The monoalcohol can be selected from ethanol, methanol, 1-butanol or isomers thereof, 1-propanol or isomers thereof, 1-pentanol or isomers thereof, or 1-hexanol and isomers thereof. Alternatively, the fatty acid alkyl esters can be produced from the trans-esterification reaction between triglycerides and monoalcohol.

The fatty acid alkyl esters then undergo fractionation by distillation where most of the saturated esters, such as, palmitic and stearic esters will be removed or partially removed from the mixture. After this, the fractionated fatty acid alkyl esters are subjected to oxidative ozonolysis where all available double bonds in the unsaturated acids will be broken down to produce mixtures of ozone esters containing mixtures of half esters of azelaic acid and $C_3$-$C_9$ monoacids and small amounts of other monoacids. Theoretically, the oxidative ozonolysis would occur at near ambient temperatures using nonanoic acid as the reaction solvent to produce intermediate ozonides. The ozonides are pumped into a secondary oxidizer unit operating at approximately 100° C. where oxygen will be passed through to generate a mixture of ozone esters. Specifically, the mixture of ozone esters includes an Azelaic hemiester; $C_3$, $C_6$, and $C_9$ monoacids; and palmitic and stearic alkyl esters.

Subsequently, the mixture of ozone esters is simultaneously esterified and trans-esterified with primary polyols to form ester polyols. The primary polyol may be selected from glycerin, trimethylolpropane, pentaerythritol, 1,2-propylene glycol, 1,3-propylene glycol, 2-methyl-1,3-propanediol, 1,4-butanediol, ethylene glycol, glucitol fructose, glucose, sucrose, aldoses, ketoses, alditols, disaccharides, or combinations thereof. The esterification and transesterification reactions are solventless and conducted by distillation of the water and monoalcohol produced by esterification and transesterification of the reaction mixture, respectively, using reduced pressure, an inert gas sparge, or a combination thereof while using an esterification/transesterification catalyst. The esterification and transesterification catalysts are solids and selected from tin oxide and tin oxalate. They are removed from the reaction mixture by filtration. The monoalcohol is removed during this step and would be recycled for continued use. The use of a mixture of ozone esters provides property advantages and also eliminates the need to fractionate the various ozone esters from each other prior to simultaneous esterification and trans-esterification. However, if a further decreased saturated acid (e.g., palmitic and stearic acid) content is desired in the ozone esters, the mixture of ozone esters may be fractionated after oxidative ozonolysis, as shown in FIG. 3.

Figure 3:
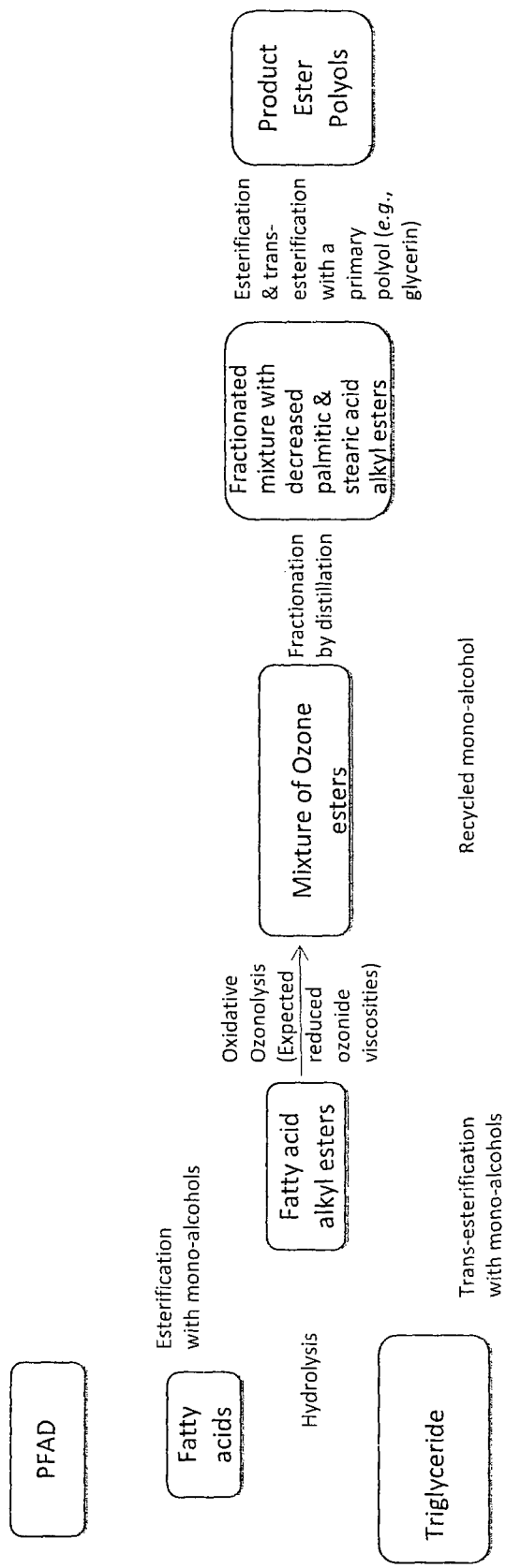
FIG. 3 is a simplified block diagram illustrating the general process of producing ester polyols via ozonolysis of fatty acid alkyl esters to form a mixture of ozone esters. The mixture of ozone esters is then fractionated by distillation to reduce saturation level in the ester mixture. The fractionated mixture of ozone esters is then simultaneously esterified and trans-esterified with a primary polyol to form the ester polyol.

FIG. 3 shows that the step for fractionation by distillation occurs after oxidative ozonolysis of the fatty acid alkyl esters. As a result, the fractionated mixture of ozone esters has a much decreased amount of the saturated fatty acid alkyl esters especially palmitic and stearic esters.

The fatty acid alkyl esters (produced from the reaction between fatty acids and a monoalcohol, e.g., butanol) are subjected to oxidative ozonolysis where mixture of ozone esters is produced through this process step. The saturated fraction of the ozone esters are then fractionated (partially removed) by distillation to reduce the level of saturation of the ozone esters (decreased level of palmitic and stearic alkyl esters). Similarly, the resultant ozone esters are then simultaneously esterified and trans-esterified with a primary polyol (e.g., glycerin, trimethylolpropane, etc.) to produce the desired ester polyols.

Further, the present invention also provides at least one ester polyol obtained or obtainable from the method according to any aspect of the invention.

The present invention also relates to an article of manufacture including the ester polyol according to the present invention. The article of manufacture may be used for, but not limited to, polyurethane based applications, polyester applications and lubricants.

The present invention also relates to a coating or foam including the ester polyol according to the invention. For example, the coating or foam may include a polyurethane coating or foam produced from the ester polyol according to the invention.

The subject matter claimed herein is not limited to embodiments that solve any disadvantages or that operate only in environments such as those described above. Rather, this background is only provided to illustrate on exemplary technology area where some embodiments described herein may be practiced. Bibliographic references mentioned in the present specification are for convenience listed in the form of a list of references and added at the end of the examples. The whole content of such bibliographic references is herein incorporated by reference.

REFERENCES

1. WO2007027223
2. U.S. Pat. No. 2,813,113

The invention claimed is:

1. A method for producing a product ester polyol, comprising:
hydrolyzing at least one triglyceride to produce at least one fatty acid;
esterifying the at least one fatty acid with at least one monoalcohol to form at least one fatty acid alkyl ester;
performing fractionation by distillation of the at least one fatty alkyl acid ester to partially remove saturates from the at least one fatty alkyl acid ester;
subjecting the at least one fractionated fatty alkyl acid ester to ozonolysis to produce a mixture of ozone esters; and
simultaneously esterifying and transesterifying the mixture of ozone esters with a primary polyol to produce a product ester polyol.

2. A method for producing a product ester polyol, comprising:
hydrolyzing at least one triglyceride to produce at least one fatty acid;
esterifying the at least one fatty acid with at least one monoalcohol to form at least one fatty acid alkyl ester;
subjecting the at least one fatty acid alkyl ester to ozonolysis to produce a mixture of ozone esters;
performing fractionation by distillation of the mixture of ozone esters to partially remove saturates from the mixture of ozone esters; and
simultaneously esterifying and transesterifying the mixture of fractionated ozone esters with a primary polyol to produce a product ester polyol.

3. The method according claim 2, wherein the at least one monoalcohol comprises methanol, ethanol, 1-propanol or isomers thereof, 1-butanol or isomers thereof, 1-pentanol or isomers thereof, or 1-hexanol or isomers thereof.

4. The method according to claim 3, wherein the at least one monoalcohol is methanol, 1-butanol, or 1-hexanol.

5. The method according to claim 2, wherein the triglyceride comprises a vegetable oil, animal fat, or a mixture thereof.

6. The method according to claim 5, wherein the vegetable oil is selected from the group consisting of soybean, safflower, linseed, corn, sunflower, olive, canola, sesame, cottonseed, mustard, camelina, jatropha, peanut, coconut, rapeseed, Chinese tallow, tung, castor, algae, wheat germ, soya, hemp, and palm oil and the animal fat is selected from the group consisting of fish oil, lard, duck fat, butter, beef tallow, pig tallow, and a mixture thereof.

7. The method according to claim 2, wherein the saturates comprise palmitic and stearic esters.

8. The method according to claim 2, wherein the triglyceride is selected from the group consisting of palm oil, olein, palm fatty acid distillate (PFAD), and palm kernel fatty acid distillate (PKFAD).

9. The method according to claim 8 further comprising:
transesterifying the triglyceride with a monoalcohol to produce the at least one fatty acid alkyl ester, the triglyceride being palm oil or olein.

10. The method according to claim 2, wherein the primary polyol is selected from the group consisting of glycerin, trimethylolpropane, pentaerythritol, 1,2-propylene glycol, 1,3-propylene glycol, 2-methyl-1,3-propanediol, 1,4-butanediol, ethylene glycol, glucitol fructose, glucose, sucrose, aldoses, ketoses, alditols, disaccharides, and combinations thereof.

11. The method according to claim 1, wherein the at least one monoalcohol comprises methanol, ethanol, 1-propanol or isomers thereof, 1-butanol or isomers thereof, 1-pentanol or isomers thereof, or 1-hexanol or isomers thereof.

12. The method according to claim 1, wherein the at least one monoalcohol is methanol, 1-butanol, or 1-hexanol.

13. The method according to claim 1, wherein the triglyceride comprises a vegetable oil, animal fat, or a mixture thereof.

14. The method according to claim 13, wherein the vegetable oil is selected from the group consisting of soybean, safflower, linseed, corn, sunflower, olive, canola, sesame, cottonseed, mustard, camelina, jatropha, peanut, coconut, rapeseed, Chinese tallow, tung, castor, algae, wheat germ, soya, hemp, and palm oil and the animal fat is selected from the group consisting of fish oil, lard, duck fat, butter, beef tallow, pig tallow, and a mixture thereof.

15. The method according to claim 1, wherein the saturates comprise palmitic and stearic esters.

16. The method according to claim 1, wherein the triglyceride is selected from the group consisting of palm oil, olein, palm fatty acid distillate (PFAD), and palm kernel fatty acid distillate (PKFAD).

17. The method according to claim 16 further comprising:
transesterifying the triglyceride with a monoalcohol to produce the at least one fatty acid alkyl ester, the triglyceride being palm oil or olein.

18. The method according to claim 1, wherein the primary polyol is selected from the group consisting of glycerin, trimethylolpropane, pentaerythritol, 1,2-propylene glycol, 1,3-propylene glycol, 2-methyl-1,3-propanediol, 1,4-butanediol, ethylene glycol, glucitol fructose, glucose, sucrose, aldoses, ketoses, alditols, disaccharides, and combinations thereof.

* * * * *